US012300368B1

(12) United States Patent
Engman et al.

(10) Patent No.: US 12,300,368 B1
(45) Date of Patent: May 13, 2025

(54) ANALYSIS AND PRESENTATION OF AGGREGATED PATIENT AND DEVICE DATA WITHIN A SYSTEM THAT INCLUDES A MEDICAL DEVICE

(71) Applicant: West Affum Holdings DAC, Dublin (IE)

(72) Inventors: Zoie R. Engman, Kirkland, WA (US); Jonathan P. Niegowski, Issaquah, WA (US); Steven E. Sjoquist, Lynnwood, WA (US)

(73) Assignee: West Affum Holdings DAC, Dublin (IE)

( * ) Notice: Subject to any disclaimer, the term of this patent is extended or adjusted under 35 U.S.C. 154(b) by 122 days.

(21) Appl. No.: 16/812,209

(22) Filed: Mar. 6, 2020

Related U.S. Application Data

(60) Provisional application No. 62/815,938, filed on Mar. 8, 2019, provisional application No. 62/815,292, filed on Mar. 7, 2019.

(51) Int. Cl.
*G16H 15/00* (2018.01)
*A61N 1/04* (2006.01)
*G16H 40/67* (2018.01)

(52) U.S. Cl.
CPC ............. *G16H 15/00* (2018.01); *A61N 1/046* (2013.01); *A61N 1/0484* (2013.01); *G16H 40/67* (2018.01)

(58) Field of Classification Search
CPC ........ G16H 10/00; G16H 10/40; G16H 15/00; G16H 20/00; G16H 20/10; G16H 20/13; G16H 20/17; G16H 30/00; G16H 40/00; G16H 50/00; G16H 70/00; G16H 40/67; G16H 80/00; G06Q 50/22–24; A61N 1/046; A61N 1/0484

USPC .................................................. 705/3, 2, 20
See application file for complete search history.

(56) References Cited

U.S. PATENT DOCUMENTS

| 3,724,355 A | 4/1973 | Busch et al. |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |

(Continued)

FOREIGN PATENT DOCUMENTS

WO          9839061 A2      9/1998

OTHER PUBLICATIONS

Heartstart MRx and XL AED Algorithm—Application Note, Jul. 2001, Edition 2 Philips Healthcare, USA.

(Continued)

*Primary Examiner* — Robert W Morgan
*Assistant Examiner* — Charles P Coleman
(74) *Attorney, Agent, or Firm* — Spectrum IP Law Group LLC

(57) ABSTRACT

In one example, a method to aggregate information from one or more medical devices comprises collecting information from one or more medical devices used by a patient, aggregating the information from the one or more medical devices into a patient record, storing the patient record to be accessible by a care station server, and providing access to the patient record to via the care station server. Other examples and related methods and apparatuses are also disclosed herein.

20 Claims, 9 Drawing Sheets

COMPONENTS OF SAMPLE WCD
SYSTEM AND NON-INVASIVE BLOOD
PRESSURE MONITOR

(56) References Cited

U.S. PATENT DOCUMENTS

| | | | |
|---|---|---|---|
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,474,574 A | 12/1995 | Payne et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,099,715 B2 | 8/2006 | Korzinov et al. | |
| 7,212,850 B2 | 5/2007 | Prystowsky et al. | |
| 7,559,902 B2 | 7/2009 | Ting et al. | |
| 7,587,237 B2 | 9/2009 | Korzinov et al. | |
| 7,865,238 B2 | 1/2011 | Brink | |
| 7,870,761 B2 | 1/2011 | Valentine et al. | |
| 7,907,996 B2 | 3/2011 | Prystowsky et al. | |
| 7,941,207 B2 | 5/2011 | Korzinov | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,579,516 B2 | 2/2017 | Kaib et al. | |
| 9,592,403 B2 | 3/2017 | Sullivan | |
| 11,013,409 B2 | 5/2021 | Kaib et al. | |
| 11,083,906 B2 * | 8/2021 | Foshee | A61N 1/3993 |
| 11,103,145 B1 | 8/2021 | Sharma et al. | |
| 11,103,717 B2 * | 8/2021 | Sullivan | A61N 1/3993 |
| 11,154,230 B2 * | 10/2021 | Sullivan | A61B 5/6805 |
| 11,160,990 B1 * | 11/2021 | Sullivan | A61N 1/0484 |
| 11,191,971 B2 * | 12/2021 | Lu | A61N 1/046 |
| 11,198,015 B2 * | 12/2021 | Breske | A61N 1/3993 |
| 11,219,373 B2 | 1/2022 | Eggers et al. | |
| 11,324,405 B2 | 5/2022 | Robinson et al. | |
| 2002/0181680 A1 * | 12/2002 | Linder | A61B 5/0006 |
| | | | 379/106.02 |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson et al. | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 * | 7/2012 | Reid | G06Q 10/10 |
| | | | 705/3 |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0073486 A1 | 3/2014 | Ahmed et al. | |
| 2014/0163663 A1 | 6/2014 | Poddar et al. | |
| 2014/0324112 A1 | 10/2014 | Macho et al. | |
| 2014/0378786 A1 | 12/2014 | Hong et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2018/0185662 A1 | 7/2018 | Foshee, Jr. et al. | |
| 2018/0242875 A1 | 8/2018 | Volpe et al. | |
| 2019/0110755 A1 | 4/2019 | Capodilupo et al. | |
| 2019/0159696 A1 * | 5/2019 | Meeker | A61N 1/025 |
| 2019/0282178 A1 | 9/2019 | Volosin et al. | |
| 2019/0329054 A1 * | 10/2019 | Breske | A61B 5/361 |
| 2020/0027568 A1 * | 1/2020 | Foshee, Jr. | G06F 13/20 |
| 2020/0121251 A1 | 4/2020 | Weber et al. | |
| 2020/0206518 A1 | 7/2020 | Freeman et al. | |
| 2020/0230428 A1 * | 7/2020 | Engman | G06F 8/10 |
| 2020/0281479 A1 * | 9/2020 | Engman | A61N 1/37247 |
| 2021/0050111 A1 * | 2/2021 | Engman | A61N 1/3987 |
| 2021/0370079 A9 * | 12/2021 | Engman | G16H 20/30 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

IFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Elias Ebrahimzadeh et al., A novel approach to predict sudden cardiac death (SCD) using nonlinear and time-frequency analyses from HRV signals, PubMed, Feb. 4, 2014, pp. 1-14, vol. 9, Issue 2, PLOS One, Tehran, Iran.

\* cited by examiner

SAMPLE COMPONENTS OF EXTERNAL DEFIBRILLATOR

COMPONENTS OF SAMPLE WCD SYSTEM AND NON-INVASIVE BLOOD PRESSURE MONITOR

ANALYSIS AND PRESENTATION OF AGGREGATED PATIENT AND DEVICE DATA WITHIN A SYSTEM THAT INCLUDES A MEDICAL DEVICE

CROSS-REFERENCE TO RELATED APPLICATIONS

The present application claims the benefit of U.S. Provisional Application No. 62/815,292 filed Mar. 7, 2019 and the benefit of U.S. Provisional Application No. 62/815,938 filed Mar. 8, 2019. Said Application No. 62/815,292 and said Application No. 62/815,938 are hereby incorporated herein by reference in their entireties.

BACKGROUND

In the state-of-the-art medical technology, advances have been made in portable and wearable devices, both medical devices and non-medical devices, that are able to monitor one or more physiological parameters of a person or a patient. Such electronic devices can gather a large amount of user, patient and/or device data for storage in the local device and/or for transmission of the data to a remote server or terminal. The data from multiple devices and multiple users or patients can be aggregated in the remote server to be processed, accessed, viewed, and analyzed for higher-level monitoring of the condition of the user or patient, and also of the operation and performance of the devices themselves.

The collected data can be aggregated in a remote server such as a cloud server that is accessible locally by a station that is directly coupled with the server, or that is accessible remotely over the Internet by a remote station. Appropriate medical personnel or technicians can then monitor the user or patient and the device while the device is deployed in the field and being used by the patient. An example of a wearable device that is capable of being remotely monitored when worn by a user or patient can be a wearable cardioverter defibrillator (WCD). Other devices can include wearable or portable heart rate monitors, pulse oximeters, electrocardiograph (ECG) machines, perspiration monitors, digital stethoscopes, or blood pressure monitors, among others.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 1:
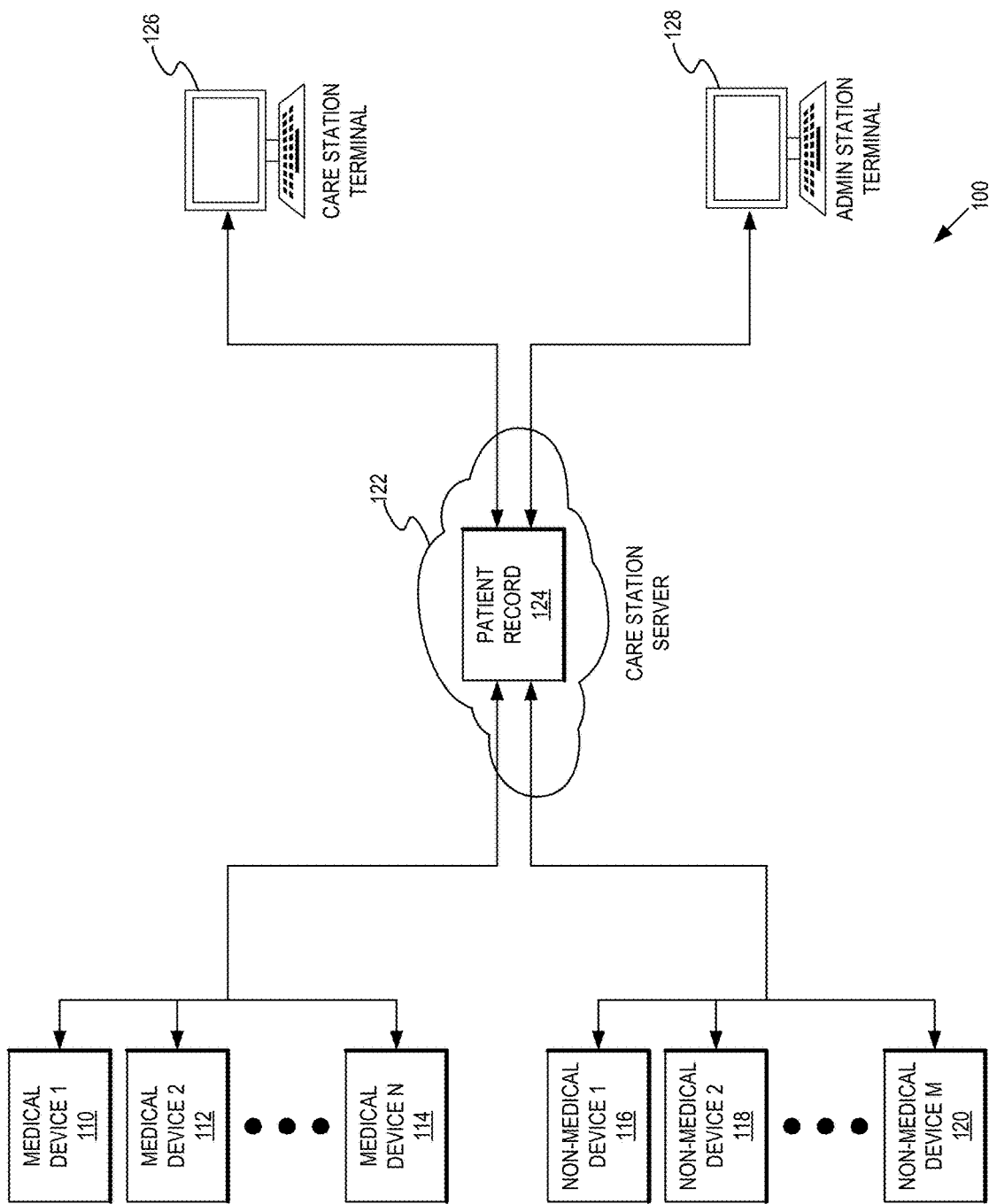
FIG. 1 is a diagram of system in which a care station server that aggregates data from multiple medical devices and multiple non-medical devices in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Referring now to FIG. 1, a diagram of system in which a care station server that aggregates data from multiple medical devices and multiple non-medical devices in accordance with one or more embodiments will be discussed. As shown in FIG. 1, system 100 can include a care station server 122 configured to couple with one or more medical devices including a first medical device (Medical Device 1) 110, a second medical device (Medial Device 2) 112, up to an Nth medical device (Medical Device N) 114. Examples of medical devices include a wearable cardioverter defibrillator (WCD), blood pressure monitor, heart rate monitor, pulse oximeter, digital stethoscope, perspiration monitor, electrocardiogra monitor, and so on. In addition, the care station server 122 can couple with one or more non-medical devices including a first non-medical device (Non-Medical Device 1) 116, a second non-medical device (Non-Medical Device 2) 118, up to an Mth medical non-medical device (Non-Medical Device M) 120. Examples of non-medical devices include a computer, smartphone, tablet, smart watch, and so on. In one or more embodiments, care station sever 122 can receive data from one or more of the medical devices or one or more of the non-medical devices and can aggregate the data in the cloud or a network to provide access to the aggregated data from designated users coupled with the care station server 122.

In one or more embodiments, a care station terminal 126 or an admin station terminal 128, or combinations thereof, can couple with the care station server 122. The care station server 122 can be configured to provide data management and configuration support for the one or more medical devices or the one or more non-medical devices, or a combination thereof. In some embodiments, the care station server 122 can be configured to collect and store both patient data and device data in a patient record 124 and to allow one or more devices, systems, or personnel to access the data in the patient record 124 in various ways as discussed herein.

In some embodiments, the aggregated data can be referred to as, or can be stored in, the patient record 124, for example when the data is obtained from an individual patient. The patient data can be aggregated in a way to provide a more complete picture of the patient to manage the patient and to manage the medical devices or the non-medical devices or a combination thereof. Examples of such aggregated patient data that can be stored in a patient record 124 can include patient activity, patient heart rate, device usage, heart condition episodes, device parameters, device information such as software version, serial number, and so on, device faults, device logs, patient events, counters, record of patient setup steps, or patient symptoms, among other data. In some examples, one of the medical devices can include a wearable cardioverter defibrillator (WCD) as discussed further herein, and the patient record 124 can include information regarding the use and operation of the WCD, and any data that can be detected or obtained by the WCD in including for example electrocardiogram (ECG) data, heart rate data, perspiration, or heart episodes, applications of therapeutic shock to the patient by the WCD, or near applications of therapeutic shock to the patient by the WCD, among other data. In some examples, data from multiple sources including the medical devices or non-medical devices can be aggregated and stored in the care station server 122 or a similar cloud based server or network to allow a cohesive and useful display of the data for patient tracking and device tracking while the patient is wearing the WCD. For example, the cohesive and useful display of the data can be displayed on a display device of the care station terminal 126 to allow the proper personnel to manage the patient and the devices and to act as needed or when appropriate.

In some embodiments, a care station terminal 126 coupled with the care station server 122 can be configured to enable health care professionals including clinical users and patient service representatives (PSRs) to access to data in patient record 124 for patients under their care or supervision, and to provide the capability to view diagnostics, episodes, wear compliance, patient activity, among other things, relating to the patient's use of the one or more medical devices or the one or more non-medical devices. In some embodiments, the admin station 128 coupled with the care station server 122 can be configured to allow users to establish and maintain various operational aspects of the system 100, including for example managing user accounts, roles and permissions, providing technical support for patients, or providing emergency response support for patients, among other aspects. An example of how the aggregated data stored in the care station server 122 can be utilized is shown in and described with respect to FIG. 2, below, In some examples, any one or more of the medical devices, the non-medical devices, the care station server 122, the care station terminal 126, or the admin station terminal 128 can comprise a machine or computing platform comprising a processor and a memory coupled with the processor. The memory can include instructions thereon to configure the processor to perform any of the methods or operations described herein. In some examples, the methods or operations can be stored on a non-transitory machine readable or computer readable medium that, when the instructions are executed by the processor, configure the processor to perform any of the methods or operations described herein.

Figure 2:
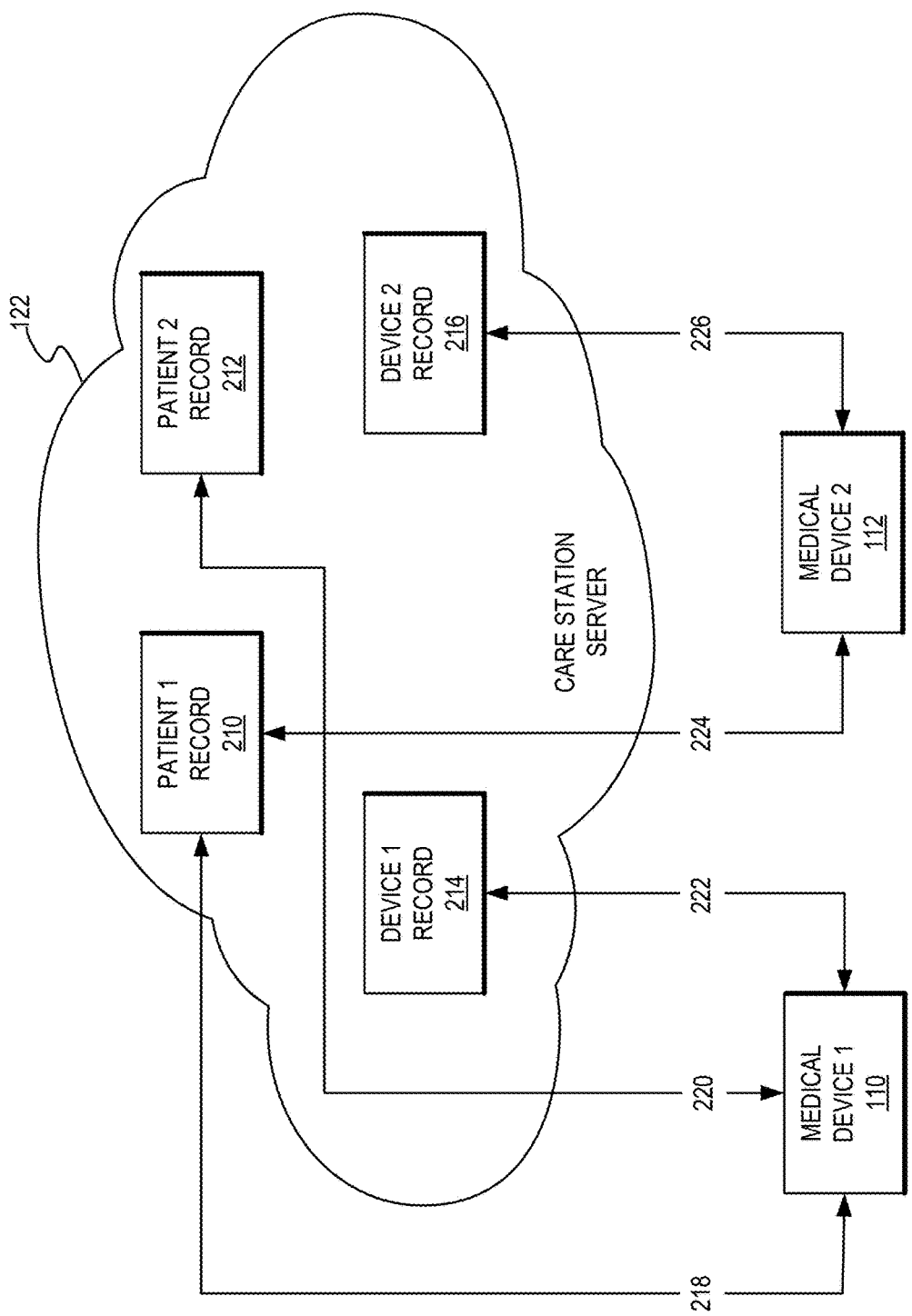
FIG. 2 is a diagram illustrating how a care station server can store data from two or more medical devices for multiple patients in accordance with one or more embodiments.

Referring now to FIG. 2, a diagram illustrating how a care station server is capable of storing data from two or more medical devices in accordance with one or more embodiments will be discussed. In some examples, the data aggregated by the care station server 122 can be accessible in at least two ways, for example by the patient record 124 as shown in FIG. 1, or the device record. FIG. 2 shows an example of how aggregated data can be obtained from two medical devices, medical device 110 and medical device 112. In some examples, the data aggregated from the two medical devices can be stored in the care station server 122 as database entries. These database entries can be accessible through the care station terminal 126 or the admin station terminal 128. The care station server 122 can be configured in several ways.

One example of how the care station server 122 can be configured overtime with multiple patients and multiple devices is described as follows. Medical device 110 can be linked to the record of a first patient record (Patient 1 Record) 210 via connection 218. If medical device 110 needs to be replaced, connection 224 shows that medical device 112 can replace medical device 110 and can be linked to the first patient record 210. The first patient record 210 now can contain all relevant patient centric information from both medical device 110 and medical device 112. For instance, the heart rate trend stored in the first patient record 210 can contain heart rate information from both medical devices. Connection 220 shows that medical device 110 can then be returned to the field and linked with a second patient to provide data to be stored in a second patient record (Patient 2 Record) 212.

Connection 222 shows that medical device 110 can be linked to a first device record (Device 1 Record) 214. All or nearly all the device centric information for medical device 110 can be stored in this record independent of which patient is wearing medical device 110. For example, event logs and device counters from both wear periods for Patient 1 and for Patient 2 can be stored in device record 214. Similarly, connection 226 shows that medical device 112 can be linked to a second device record (Device 2 record) 216.

Another example of how the care station server 122 can be configured over time with multiple patients and multiple devices can be as follows. In this example, medical device 110 can be a first WCD that is prescribed to and linked to Patient 1. The data obtained from the use and operation of the first WCD can be stored in patient record 210 and in device record 214. When the prescription for Patient 1 ends, Patient 1 can be prescribed a second WCD referred to as medical device 112. The same patient record 210 as used by medical device 110 can be continued and used by the second WCD, medical device 112. The data for the second WCD can be stored in device record 216.

In one or more embodiments, care station server 122 can aggregate information from a plurality of wearable cardioverter defibrillators (WCDs) 310 as discussed in further detail below, for example in FIG. 3. Information can be collected from the plurality of WCDs used by a patient. The WCD 310 customized and fitted to a particular patient. The information two or more WCDs of the plurality of WCDs can be aggregated into a patient record. For example, medical device 110 can comprise a first WCD and medical device 112 can comprise a second WCD. Information can be collected by both WCDs and combined into the patient record 210 for the patient. The patient record 210 can be stored in care station server 122, and the care station server 122 can provide access to the patient record 210 via the care station server 122. In some embodiments, access to the patient record 210 can be provided via a processor care station server 122. In some examples, the patient wears the first WCD for a first period of time, and the second WCD for a second period of time. In some examples, the second WCD is used by the patient responsive to the first WCD having an error condition. In some examples, the second WCD can replace the first WCD, for example when the first WCD experiences a fault, a failure, or an error condition. In other examples, the first WCD can be worn, and the second WCD can be worn, for example to compare the operation of the first WCD with the second WCD. In further examples, the performance of one or more medical devices can be monitored remotely from the patient via accessing the patient record 210. Such device monitoring can be done in addition to, separately from, or combined with monitoring the patient himself or herself. It should be noted that these are merely examples of combining or aggregating the data of two medical devices such as two WCDs into a single patient record, and the scope of the disclosed subject matter is not limited in these respects.

Figure 3:
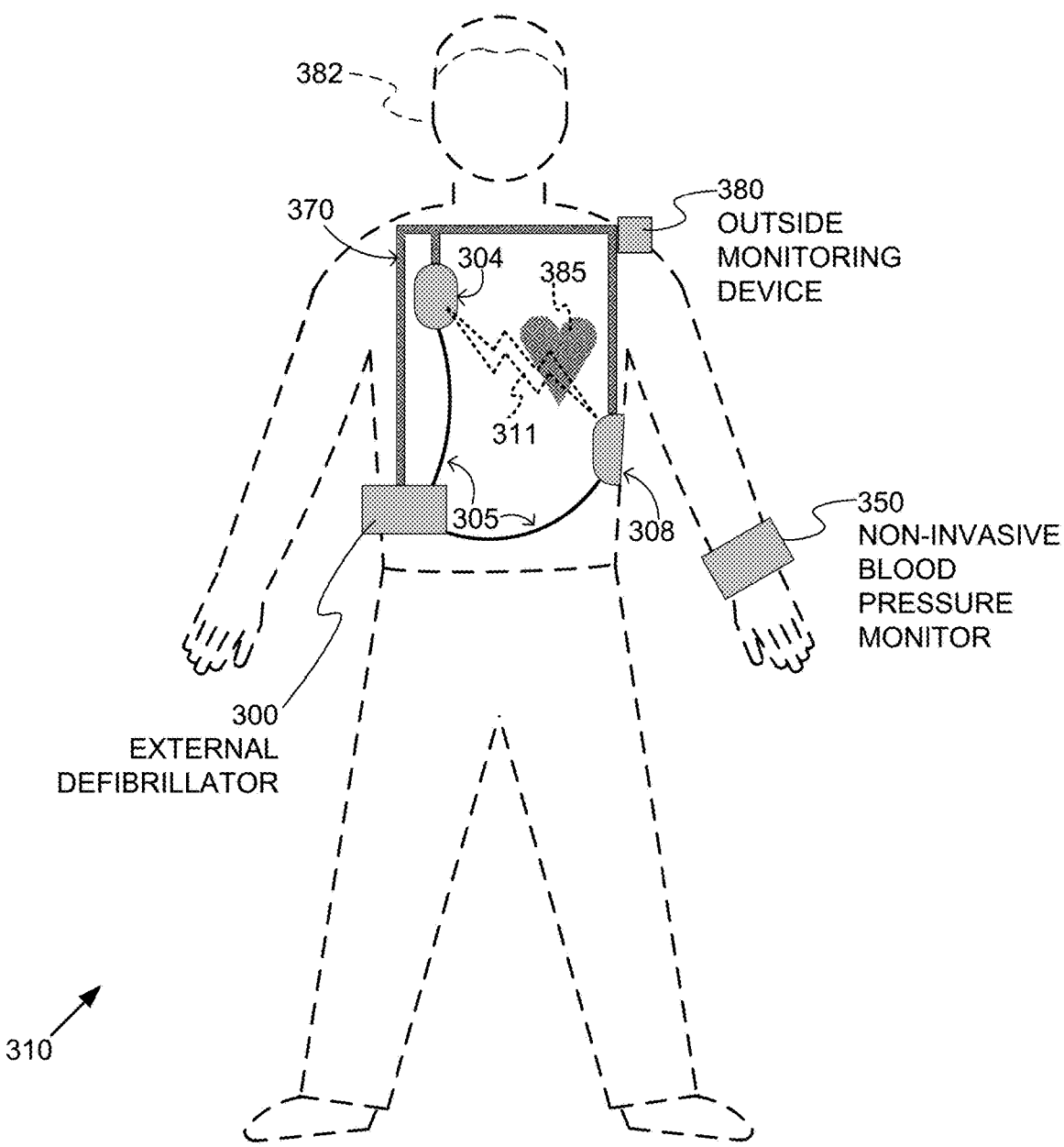
FIG. 3 is a diagram of components of a sample wearable cardioverter defibrillator (WCD) system incorporating a non-invasive blood pressure (NIBP) monitor in accordance with one or more embodiments.

FIG. 3 is a diagram of components of example medical devices as shown in FIG. 1 and FIG. 2 that can include a wearable cardioverter defibrillator (WCD) system and a non-invasive blood pressure (NIBP) monitor in accordance with one or more embodiments. It should be noted that a WCD and an NIBP are discussed herein for purposes of example, and the scope of the claimed disclosure is not limited in these respects. A wearable cardioverter defibrillator (WCD) system 310 according to embodiments may protect an ambulatory patient by electrically restarting his or her heart if needed. Such a WCD system 310 may have several components. These components can be provided separately as modules that can be interconnected, or can be combined with other components, and so on.

FIG. 3 also depicts a patient 382. Patient 382 may also be referred to as a person and/or wearer, since the patient is wearing components of the WCD system 310. Patient 382 is ambulatory, which means that, while wearing the wearable portion of the WCD system 310, patient 382 can walk around and is not necessarily bed-ridden. While patient 382 can also be a "user" of the WCD system 310, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The context of these and other related terms within this description should be interpreted accordingly.

A WCD system 310 according to embodiments can be configured to defibrillate the patient 382 who is wearing the designated parts the WCD system 310. Defibrillating can be by the WCD system 310 delivering an electrical charge to the patient's body in the form of an electric shock. The electric shock can be delivered in one or more pulses.

FIG. 3 also depicts components of a WCD system 310 made according to embodiments. One such component is a support structure 370), or garment, that is wearable by ambulatory patient 382. Accordingly, support structure 370) is configured to be worn by ambulatory patient 382 for at least several hours per day, and for at least several days, even a few months. It will be understood that support structure 370) is shown only generically in FIG. 3, and in fact partly conceptually. FIG. 3 is provided merely to illustrate concepts about support structure 370, and is not to be construed as limiting how support structure 370 is implemented, or how it is worn.

Support structure 370 can be implemented in many different ways. For example, it can be implemented in a single component or a combination of multiple components. In embodiments, support structure 370) could include a vest, a half-vest, a garment, etc. In such embodiments such items can be worn similarly to analogous articles of clothing. In embodiments, support structure 370 could include a harness, one or more belts or straps, etc. In such embodiments, such items can be worn by the patient around the torso, hips, over the shoulder, etc. In embodiments, support structure 370 can include a container or housing, which can even be waterproof. In such embodiments, the support structure can be worn by being attached to the patient's body by adhesive material, for example as shown and described in U.S. Pat. No. 8,024,037 which is incorporated herein by reference in its entirety. Support structure 370 can even be implemented as described for the support structure of U.S. application Ser. No. 15/120,655, published as US 2017/0056682 A1, which is incorporated herein by reference in its entirety. In such embodiments, the person skilled in the art will recognize that additional components of the WCD system 310 can be in the housing of a support structure instead of being attached externally to the support structure, for example as described in the US 2017/0056682 A1 document. There can be other examples.

FIG. 3 also shows a sample external defibrillator 300. As described in more detail later in this document, some aspects of external defibrillator 300 include a housing and an energy storage module within the housing. As such, in the context of a WCD system 310, defibrillator 300 is sometimes called a main electronics module or a monitor. The energy storage module can be configured to store an electrical charge. Other components can cause at least some of the stored electrical charge to be discharged via electrodes through the patient to deliver one or more defibrillation shocks through the patient 382.

FIG. 3 also shows sample defibrillation electrodes 104 and/or 308, which are coupled to external defibrillator 300 via electrode leads 305. Defibrillation electrodes 104 and/or 308 can be configured to be worn by patient 382 in several ways. For instance, defibrillator 300 and defibrillation electrodes 104 and/or 308 can be coupled to support structure 370, directly or indirectly. In other words, support structure 370 can be configured to be worn by ambulatory patient 382 to maintain at least one of electrodes 104 and/or 308 on the body of ambulatory patient 382, while patient 382 is moving around, etc. The electrode can be thus maintained on the body by being attached to the skin of patient 382, simply pressed against the skin directly or through garments, etc. In some embodiments the electrode is not necessarily pressed against the skin, but becomes biased that way upon sensing a condition that could merit intervention by the WCD system 310. In addition, many of the components of defibrillator 300 can be considered coupled to support structure 370 directly, or indirectly via at least one of defibrillation electrodes 104 and/or 308.

When defibrillation electrodes 104 and/or 308 make good electrical contact with the body of patient 382, defibrillator 300 can administer, via electrodes 104 and/or 308, a brief, strong electric pulse 311 through the body. Pulse 311 is also known as shock, defibrillation shock, therapy, electrotherapy, therapy shock, etc. Pulse 311 is intended to go through and restart heart 385, in an effort to save the life of patient 382. Pulse 311 can further include one or more pacing pulses of lesser magnitude to simply pace heart 385 if needed, and so on.

A typical defibrillator decides whether to defibrillate or not based on an ECG signal of the patient. External defibrillator 300, however, may initiate defibrillation, or hold-off defibrillation, based on a variety of inputs, with the ECG signal merely being one of these inputs.

A WCD system 310 according to embodiments can obtain data from patient 382. For collecting such data, the WCD system 310 may optionally include at least an outside monitoring device 380. Device 380 is called an "outside" device because it could be provided as a standalone device, for example not within the housing of defibrillator 300. Device 380 can be configured to sense or monitor at least one local parameter. A local parameter can be a parameter of patient 382, or a parameter of the WCD system 310, or a parameter of the environment, as will be described later in this document. In some embodiments, outside monitoring device 380 can comprise a hub or similar device through which connections and/or leads may be made of the various components of the WCD system 300. For example, at least some of the leads of external defibrillator 300 may be connected to and/or routed through the outside monitoring device 380 including, for example, one or more ECG leads, a right-leg drive (RLD) lead, leads connected to the defibrillation electrodes 104 and/or 308, and so on. In some embodiments, outside monitoring device 380 can include a controller or processor that is used to implement at least a portion of the shock/no-shock algorithm to determine whether a shock should or should not be applied to the patient 382, although the scope of the disclosed subject matter is not limited in this respect.

For some of these parameters, device 380 may include one or more sensors or transducers. Each one of such sensors can be configured to sense a parameter of patient 382, and to render an input responsive to the sensed parameter. In some embodiments the input is quantitative, such as values of a sensed parameter. In other embodiments the input is qualitative, such as informing whether or not a threshold is crossed, and so on. Sometimes these inputs about patient 382 are also called physiological inputs and patient inputs. In embodiments, a sensor can be construed more broadly, as encompassing many individual sensors.

Optionally, device 380 is physically coupled to support structure 370. In addition, device 380 may be communicatively coupled with other components that are coupled to support structure 370). Such communication can be implemented by a communication module, as will be deemed applicable by a person skilled in the art in view of this description.

In embodiments, one or more of the components of the shown WCD system 310 may be customized for patient 382. This customization may include a number of aspects. For instance, support structure 370) can be fitted to the body of patient 382. For another instance, baseline physiological parameters of patient 382 can be measured, such as the heart rate of patient 382 while resting, while walking, motion detector outputs while walking, etc. The measured values of such baseline physiological parameters can be used to customize the WCD system 310, in order to make its diagnoses more accurate, since patients' bodies differ from one another. Of course, such parameter values can be stored in a memory of the WCD system 310, and so on. Moreover, a programming interface can be made according to embodiments, which receives such measured values of baseline physiological parameters. Such a programming interface may input automatically in the WCD system 310 these, along with other data.

In one or more embodiments, WCD system 310 may include a non-invasive blood pressure (NIBP) monitor 350 that can monitor the blood pressure of the patient 382 as one or more of the patient parameters collected by WCD system 310. The NIBP monitor 350 can be referred to as non-invasive since the monitor can obtain a blood pressure reading of the patient 382 without insertion of catheter into a patient's blood vessel. In some embodiments, NIBP monitor 350) can be referred to as a cuff-less NIBP monitor 350 in that it can obtain a blood pressure reading without using a conventional cuff device placed around the patient's arm that is inflated and deflated to obtain the measurement. Furthermore, the NIBP 350 monitor can obtain frequent blood pressure measurements while the patient 382 is wearing the monitor through the day and/or during the night when the patient 382 is sleeping.

The NIBP monitor 350 may be provided in various types of form factors to be placed on the patient's body at various locations and/or to integrate with WCD system 310 in various ways. For example, in some embodiments, NIBP monitor 350 may be worn on the wrist of the patient 382 or various other locations on the patient 382 such as on the arm, leg, ankle, chest, or back of the patient 382 depending on the provided form factor and/or technology utilized by the NIBP monitor 350 to obtain a blood pressure reading.

In some embodiments, NIBP monitor 350 may be incorporated into an external device or accessory such as a smartphone. Such devices may employ an optical NIBP sensor. Such devices may come in various other form factors such as a patch, watch, earring, eye glasses, ankle bracelet, and so on, wherein the NIBP monitor 350 can be unobtrusive and in location in which the patient's vasculature may be near the skin so that the optical sensor of this type of NIBP monitor 350 can obtain good readings.

In some embodiments, the NIBP monitor 350 can include an optical based NIBP sensor built into the alert button or stop button of the WCD system 310 wherein the alert button or stop button is used by the patient 382 to stop an impending shock if the patient so desires. In such embodiments, the patient is already aware of the location of the alert button or stop button which would provide a simple and readily available device for the patient to use to take a blood pressure measurement. In addition, when the NIBP monitor 350 is in the alert button or stop button, the patient's blood pressure can be obtained whenever the patient 382 needs to abort a shock.

In one or more embodiments, the NIBP monitor 350 can include or otherwise comprise an optical pulse oximetry sensor and/or a methemoglobin sensor wherein optical NIBP sensor functionality can be implemented using a pulse oximetry or methemoglobin sensor. In other embodiments, a cuff-less NIBP monitor 350 can be incorporated in one or more of the ECG electrodes of the WCD system 310. Such an NIBP sensor can be an optical sensor as described above, or an electro-mechanical sensor such as described in "*A CMOS-based Tactile Sensor for Continuous Blood Pressure Monitoring*". Kirstein, Sedivy, et al., Proceedings of the Design, Automation and Test in Europe Conference and Exhibition, 1530-1591/05 (March 2005) which is incorporated herein by reference in its entirety.

In other embodiments, the NIBP monitor 350 can be adapted for use in proposed adhesive type defibrillators as disclosed in U.S. Pat. No. 8,024,037. For example, the NIBP monitor 350 can be disposed in one of the adhesive modules as shown in the '037 patent, or in an "appendage" or "flap" that extends from the module so that the NIBP monitor 350 is positioned on an appropriate location on the patient. Embodiments of a cuff-less NIBP sensor can include a wireless communication interface such as BLUETOOTH, near-field communication (NFC), Wi-Fi DIRECT, ZIGBEE, and so on, to transmit the blood pressure data to a module of the WCD system 310, to a personal communication device of the WCD system 310 for example as disclosed in U.S. Pat. No. 8,838,235, or to another remote device. Said U.S. Pat. No. 8,838,235 is incorporated herein by reference in its entirety. In some embodiments, a wired communication link can be used instead of a wireless communication link. For example, the NIBP monitor 350 can be implemented in an electrode that can be configured so that the blood pressure data is transmitted on a wire bundled with the wire or wires of the electrode sensors, or multiplexed on the same wire as the electrode data, and so on.

Figure 4:
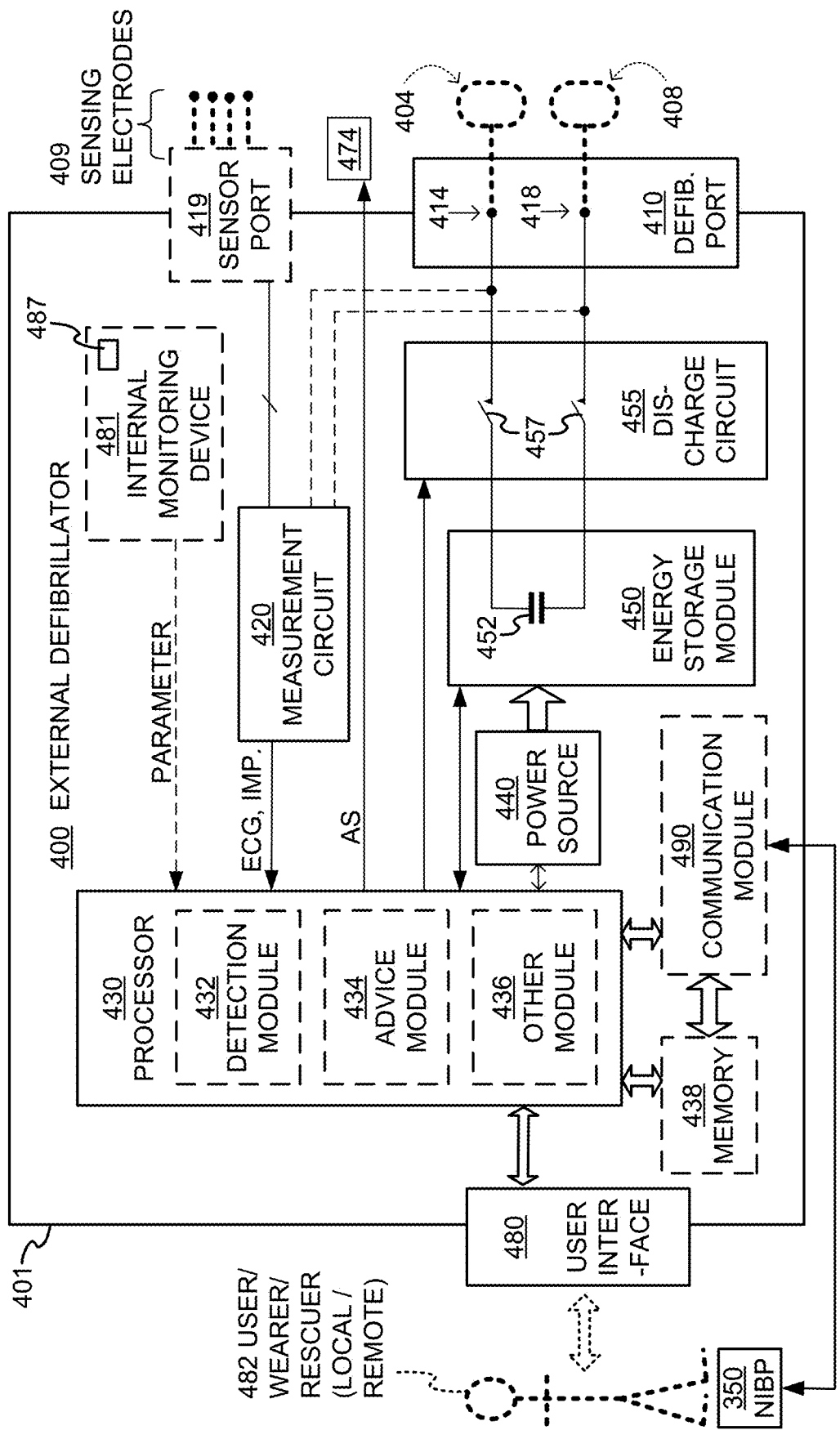
FIG. 4 is a diagram showing sample components of an external defibrillator, such as the one belonging in the system of FIG. 3, including an NIBP monitor in accordance with one or more embodiments.

FIG. 4 is a diagram showing sample components of an external defibrillator, such as the one belonging in the system of FIG. 3, including an NIBP monitor in accordance with one or more embodiments. Some components of WCD system 310 can be, for example, included in external defibrillator 300 of FIG. 3. The components shown in FIG. 4 can be provided in a housing 401, which may also be referred to as casing 401. External defibrillator 400 and NIBP monitor 350 can comprise examples of the medical devices shown in FIG. 1 and FIG. 2.

External defibrillator 400 is intended for a patient who would be wearing it, such as ambulatory patient 382 of FIG. 3. Defibrillator 400 may further include a user interface 480 for a user 482. User 482 can be patient 382, also known as wearer 382. Alternatively, user 482 can be a local rescuer at the scene, such as a bystander who might offer assistance, or a trained person. Alternatively, user 482 might be a remotely located trained caregiver in communication with the WCD system 310.

User interface 480 can be made in a number of ways. User interface 480 may include output devices, which can be visual, audible or tactile, for communicating to a user 482 by outputting images, sounds or vibrations. Images, sounds, vibrations, and anything that can be perceived by user 482 can also be called human-perceptible indications (HPIs).

There are many examples of output devices. For example, an output device can be a light, or a screen to display what is sensed, detected and/or measured, and provide visual feedback to user 482 acting as a rescuer for their resuscitation attempts, and so on. Another output device can be a speaker, which can be configured to issue voice prompts, beeps, loud alarm sounds and/or words to warn bystanders, etc.

User interface 480 further may include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock and may be referred to as a stop button in such embodiments.

Defibrillator 400 may include an internal monitoring device 481. Device 481 is called an "internal" device because it is incorporated within housing 401. Monitoring device 481 can sense or monitor patient parameters such as patient physiological parameters, system parameters and/or environmental parameters, all of which can be called patient data. In other words, internal monitoring device 481 can be complementary or an alternative to outside monitoring device 380 of FIG. 3. Allocating which of the parameters are to be monitored by which of monitoring devices 380, 481 can be done according to design considerations. Device 481 may include one or more sensors as also described elsewhere in this document.

Patient parameters may include patient physiological parameters. Patient physiological parameters may include, for example and without limitation, those physiological parameters that can be of any help in detecting by the WCD system 310 whether or not the patient is in need of a shock or other intervention or assistance. Patient physiological parameters may also optionally include the patient's medical history, event history, and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring device 380 and/or monitoring device 481 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In accordance with one or more embodiments, monitoring device 380 and/or monitoring device 481 may include a cuff-less non-invasive blood pressure (NIBP) monitor and may tangibly embody one or more embodiments of NIBP monitor 350 or may operate in conjunction with NIBP monitor 350, and the scope of the disclosed subject matter is not limited in this respect. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 482. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise: c) heart rate profile during exercise and measurement of activity vigor, such as from the profile of an accelerometer signal and informed from adaptive rate pacemaker technology: d) heart rate trending: e) perfusion, such as from SpO2, CO2, or other parameters such as those mentioned above: f) respiratory function, respiratory rate, etc.: g) motion, level of activity; and so on. Once a trend is detected, it can be stored and/or reported via a communication link, optionally along with a warning if warranted. From the report, a physician monitoring the progress of patient (user) 482 will know about a condition that is either not improving or deteriorating.

Patient state parameters include recorded aspects of patient (user) 482, such as motion, posture, whether they have spoken recently plus maybe also what they said, and so on, plus optionally the history of these parameters. Alternatively, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether sudden cardiac arrest (SCA) is indeed taking place.

A WCD system 310 made according to embodiments may thus include a motion detector 487. In embodiments, a motion detector can be implemented within monitoring device 380 or monitoring device 481. Such a motion detector can be made in many ways as is known in the art, for example by using an accelerometer. In this example, a motion detector 487 is implemented within monitoring device 481. A motion detector of a WCD system 310 according to embodiments can be configured to detect a motion event. A motion event can be defined as is convenient, for example a change in motion from a baseline motion or rest, etc. In such cases, a sensed patient parameter can include motion.

System parameters of a WCD system 310 can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed or determined, if monitoring device 380 and/or monitoring device 481 includes a GPS location sensor as described above, and if it is presumed that the patient is wearing the WCD system 310.

Defibrillator 400 typically includes a defibrillation port 410, which can be a socket in housing 401. Defibrillation port 410 includes electrical node 414 and/or electrical node 418. Leads of defibrillation electrode 404 and/or defibrillation electrode 408, such as leads 305 of FIG. 3, can be plugged into defibrillation port 410 so as to make electrical contact with node 414 and node 418, respectively. It is also possible that defibrillation electrode 404 and/or defibrillation electrode 408 instead are connected continuously to defibrillation port 410. Either way, defibrillation port 410 can be used for guiding, via electrodes, to the wearer at least some of the electrical charge that has been stored in an energy storage module 450 that is described more fully later in this document. The electric charge will be the shock for defibrillation, pacing, and so on.

Defibrillator 400 may optionally also have a sensor port 419 in housing 401, which is also sometimes known as an ECG port. Sensor port 419 can be adapted for plugging in sensing electrodes 409, which are also known as ECG electrodes and ECG leads. It is also possible that sensing electrodes 409 can be connected continuously to sensor port 419, instead. Sensing electrodes 409 are types of transducers that can help sense an ECG signal, e.g. a 12-lead signal, or a signal from a different number of leads, especially if the leads make good electrical contact with the body of the patient and in particular with the skin of the patient. As with defibrillation electrodes 404 and/or 408, the support structure 370) can be configured to be worn by patient 482 so as to maintain sensing electrodes 409 on a body of patient (user) 482. For example, sensing electrodes 409 can be attached to the inside of support structure 370 for making good electrical contact with the patient, similarly with defibrillation electrodes 404 and/or 408.

Optionally a WCD system 310 according to embodiments also includes a fluid that can be deployed automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel so that it does not flow away after being deployed from the location it is released near the electrode. The fluid can be used for both defibrillation electrodes 404 and/or 408, and for sensing electrodes 409.

The fluid may be initially stored in a fluid reservoir, not shown in FIG. 4. Such a fluid reservoir can be coupled to the support structure 370. In addition, a WCD system 310 according to embodiments further includes a fluid deploying mechanism 474. Fluid deploying mechanism 474 can be configured to cause at least some of the fluid to be released from the reservoir, and be deployed near one or both of the patient locations to which electrodes 404 and/or 408 are configured to be attached to the patient. In some embodiments, fluid deploying mechanism 474 is activated prior to the electrical discharge responsive to receiving activation signal (AS) from a processor 430, which is described more fully later in this document.

In some embodiments, defibrillator 400 also includes a measurement circuit 420, as one or more of its working together with its sensors or transducers. Measurement circuit 420 senses one or more electrical physiological signals of the patient from sensor port 419, if provided. Even if defibrillator 400 lacks sensor port 419, measurement circuit 420 optionally may obtain physiological signals through nodes 414 and/or 418 instead, when defibrillation electrodes 404 and/or 408 are attached to the patient. In these embodiments, the input reflects an ECG measurement. The patient parameter can be an ECG, which can be sensed as a voltage difference between electrodes 404 and 408. In addition, the patient parameter can be an impedance, which can be sensed between electrodes 404 and 408 and/or between the connections of sensor port 419 considered pairwise. Sensing the impedance can be useful for detecting, among other things, whether these electrodes 404 and/or 408 and/or sensing electrodes 409 are not making good electrical contact with the patient's body. These patient physiological signals may be sensed when available. Measurement circuit 420 can then render or generate information about them as inputs, data, other signals, etc. As such, measurement circuit 420 can be configured to render a patient input responsive to a patient parameter sensed by a sensor. In some embodiments, measurement circuit 420 can be configured to render a patient input, such as values of an ECG signal, responsive to the ECG signal sensed by sensing electrodes 409. More strictly speaking, the information rendered by measurement circuit 420 is output from it, but this information can be called an input because it is received as an input by a subsequent device or functionality.

Defibrillator 400 also includes a processor 430. Processor 430 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 430 may include, or have access to, a non-transitory storage medium, such as memory 438 that is described more fully later in this document. Such a memory 438 can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions to offer or fulfill a particular functionality. Embodiments of modules and the functionality delivered are not limited by the embodiments described in this document.

Processor 430 can be considered to have a number of modules. One such module can be a detection module 432. Detection module 432 can include a Ventricular Fibrillation (VF) detector. The patient's sensed ECG from measurement circuit 420, which can be available as inputs, data that reflect values, or values of other signals, may be used by the VF detector to determine whether the patient is experiencing VF. Detecting VF is useful because VF typically results in sudden cardiac arrest (SCA). Detection module 432 can also include a Ventricular Tachycardia (VT) detector, and so on.

Another such module in processor 430 can be an advice module 434, which generates advice for what to do. The advice can be based on outputs of detection module 432. There can be many types of advice according to embodiments. In some embodiments, the advice is a shock/no shock determination that processor 430 can make, for example via advice module 434. The shock/no shock determination can be made by executing a stored Shock Advisory Algorithm (SAA). A Shock Advisory Algorithm can make a shock/no shock determination from one or more ECG signals that are captured according to embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In good or ideal conditions, a very reliable shock/no shock determination can be made from a segment of the sensed ECG signal of the patient. In practice, however, the ECG signal is often corrupted by electrical noise, which can make it difficult to analyze. Too much noise sometimes causes an incorrect detection of a heart arrhythmia, resulting in a false alarm to the patient. Noisy ECG signals may be handled as described in U.S. application Ser. No. 16/037,990, filed on Jul. 17, 4018 and since published as US 4019/0030351 A1, and in U.S. application Ser. No. 16/038,007, filed on Jul. 17, 4018 and since published as US 4019/0030352 A1, both by the same applicant and incorporated herein by reference in their entireties.

Processor 430 can include additional modules, such as other module 436, for other functions. In addition, if internal monitoring device 481 is provided, processor 430 may receive its inputs, etc.

Defibrillator 400 optionally further includes a memory 438, which can work together with processor 430. Memory 438 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 438 is thus a non-transitory storage medium. Memory 438, if provided, can include programs and/or instructions for processor 430, which processor 430 may be able to read and execute. More particularly, the programs can include sets of instructions in the form of code, which processor 430 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 430, and can also include protocols and ways that decisions can be made by advice module 434. In addition, memory 438 can store prompts for user 482, if this user is a local rescuer. Moreover, memory 438 can store data. This data can include patient data, system data and environmental data, for example as learned by internal monitoring device 481 and outside monitoring device 380. The data can be stored in memory 438 before it is transmitted out of defibrillator 400, or be stored there after it is received by defibrillator 400.

Defibrillator 400 can optionally include a communication module 490, for establishing one or more wired and/or wireless communication links with other devices of other entities, such as a remote assistance center, Emergency Medical Services (EMS), and so on. The communication module 490 may include short range wireless communication circuitry for example in accordance with a BLUETOOTH or ZIGBEE standard, short or medium range wireless communication for example a W-Fi or wireless local area network (WLAN) in accordance with an Institute of Electrical and Electronics Engineers (IEEE) 802.11x standard, or a wireless wide area network (WWAN) in accordance with a Third Generation Partnership Project (3GPP) including a 3G, 4G, or 5G New Radio (NR) standard. The communication links can be used to transfer data and commands. The data may be patient data, event information, therapy attempted, cardiopulmonary resuscitation (CPR) performance, system data, environmental data, and so on. For example, communication module 490 may transmit wirelessly, e.g. on a daily basis, heart rate, respiratory rate, and other vital signs data to a server accessible over the internet, for instance as described in U.S. application Ser. No. 13/959,894 filed Aug. 6, 4012 and published as US 2014/0043149 A1 and which is incorporated herein by reference in its entirety. This data can be analyzed directly by the patient's physician and can also be analyzed automatically by algorithms designed to detect a developing illness and then notify medical personnel via text, email, phone, etc. Module 490 may also include such interconnected sub-components as may be deemed necessary by a person skilled in the art, for example an antenna, portions of a processor, supporting electronics, outlet for a telephone or a network cable, etc. Furthermore, in accordance with one or more embodiments, NIBP 350 can couple with communication module 490 of defibrillator 400 via a wired or wireless communication link. In some embodiments, NIBP 350) can couple with defibrillator 400 via outside monitoring device 380 of FIG. 3 acting as an intermediate device, connector, bus, router, switch, or hub, and the scope of the disclosed subject matter is not limited in this respect.

Defibrillator 400 also may include a power source 440. To enable portability of defibrillator 400, power source 440 typically includes a battery. Such a battery typically can be implemented as a battery pack, which can be rechargeable or not. Sometimes a combination of rechargeable and non-rechargeable battery packs is provided. Other embodiments of power source 440 can include an alternating current (AC) power override, for where AC power will be available, an energy-storing capacitor or bank of capacitors, and so on. Appropriate components may be included to provide for charging or replacing power source 440. In some embodiments, power source 440) is controlled and/or monitored by processor 430.

Defibrillator 400 additionally may include an energy storage module 450. Energy storage module 450 can be coupled to the support structure 370 of the WCD system 310, for example either directly or via the electrodes and their leads. Module 450) is where some electrical energy can be stored temporarily in the form of an electrical charge when preparing it for discharge to administer a shock. In some embodiments, module 450 can be charged from power source 440 to the desired amount of energy as controlled by processor 430. In typical implementations, module 450 includes a capacitor 452 which can be a single capacitor or a system or bank of capacitors, and so on. In some embodiments, energy storage module 450 includes a device that exhibits high power density such as an ultracapacitor. As described above, capacitor 452 can store the energy in the form of an electrical charge for delivering to the patient.

A decision to shock can be made responsive to the shock criterion being met, as per the above-mentioned determination. When the decision is to shock, processor 430 can be configured to cause at least some or all of the electrical charge stored in module 450 to be discharged through patient 382 while the support structure is worn by patient 382 so as to deliver a shock 311 to patient 382.

For causing the discharge, defibrillator 400 can include a discharge circuit 455. When the decision is to shock, processor 430 can be configured to control discharge circuit 455 to discharge through the patient 382 at least some or all of the electrical charge stored in energy storage module 450. Discharging can be to nodes 414 and/or 418, and from there to defibrillation electrodes 404 and/or 408, so as to cause a shock to be delivered to the patient. Circuit 455 can include one or more switches 457. Switches 457 can be made in a number of ways, such as by an H-bridge, and so on. Circuit 455 could also be thus controlled via processor 430, and/or user interface 480.

A time waveform of the discharge may be controlled by thus controlling discharge circuit 455. The amount of energy of the discharge can be controlled by how much energy storage module has been charged, and by how long discharge circuit 455 is controlled to remain open. Defibrillator 400 optionally can include other components.

Figure 5:
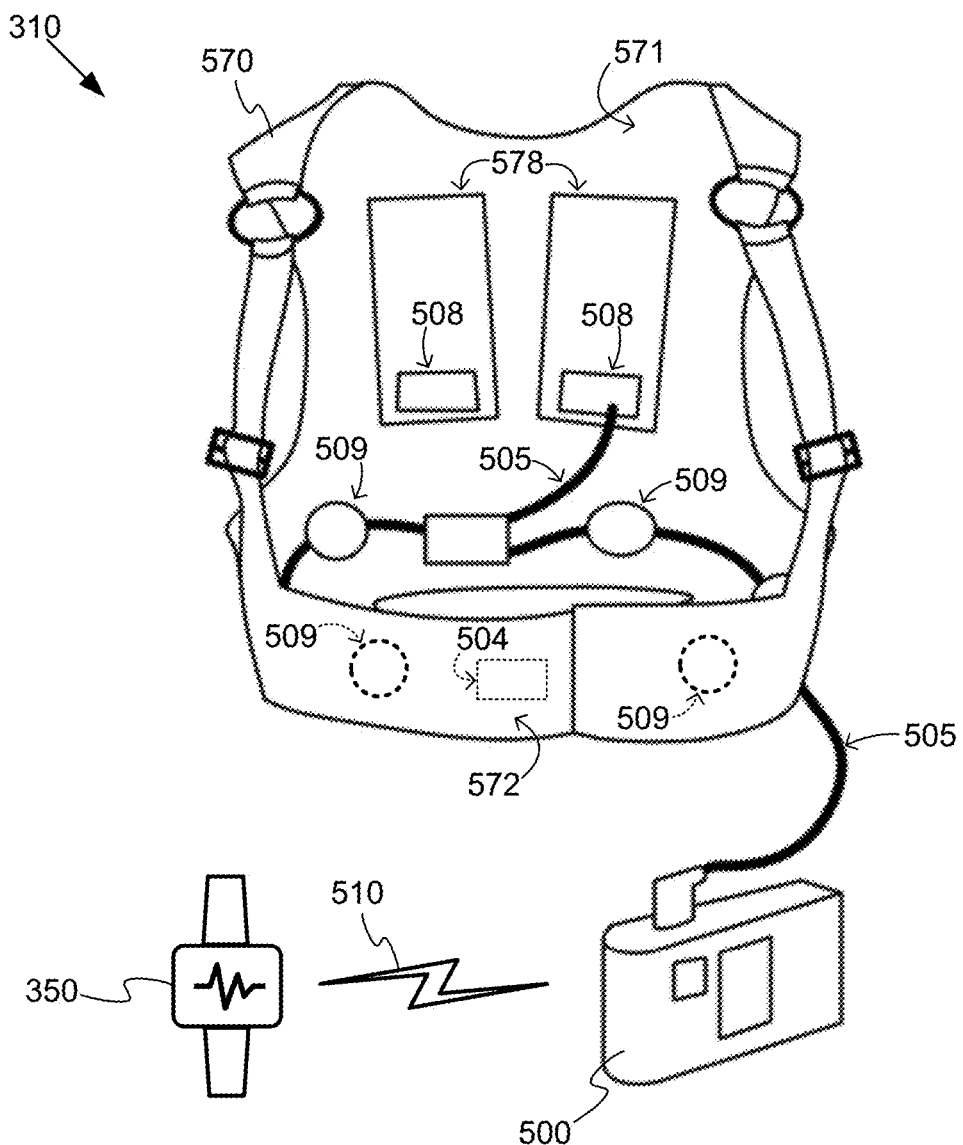
FIG. 5 is a diagram of sample embodiments of components of a WCD system and an NIBP monitor in accordance with one or more embodiments.

FIG. 5 is a diagram of example embodiments of components of a WCD system 310 and an NIBP monitor 350 in accordance with one or more embodiments. A support structure 570 includes a vest-like wearable garment. Support structure 570 has a back side 571, and a front side 572 that closes in front of the chest of the patient. WCD system 310 and NIBP monitor 350 can comprise examples of two medical devices shown in FIG. 1 and FIG. 2.

The WCD system 310 of FIG. 5 also includes an external defibrillator 500. FIG. 5 does not show any support for external defibrillator 500, which may be carried in a purse, on a belt, by a strap over the shoulder, and so on. Wires 505 connect external defibrillator 500 to electrodes 504, 508, and/or 509. Of those, electrodes 504 and 508 are defibrillation electrodes, and electrodes 509 are ECG sensing electrodes.

Support structure 570) is configured to be worn by the ambulatory patient to maintain electrodes 504, 508, and/or 509 on a body of the patient. Back defibrillation electrodes 508 can be maintained in pockets 578. The inside of pockets 578 can be made with loose netting, so that electrodes 508 can contact the back of the patient 382, especially with the help of the conductive fluid that has been deployed in such embodiments. In addition, sensing electrodes 509 are maintained in positions that surround the patient's torso, for sensing ECG signals and/or the impedance of the patient 382.

ECG signals in a WCD system 310 may include too much electrical noise to be useful. To ameliorate the problem, multiple ECG sensing electrodes 509 are provided, for presenting many options to processor 430. These options are different vectors for sensing the ECG signal, as described in more detail below.

Figure 6:
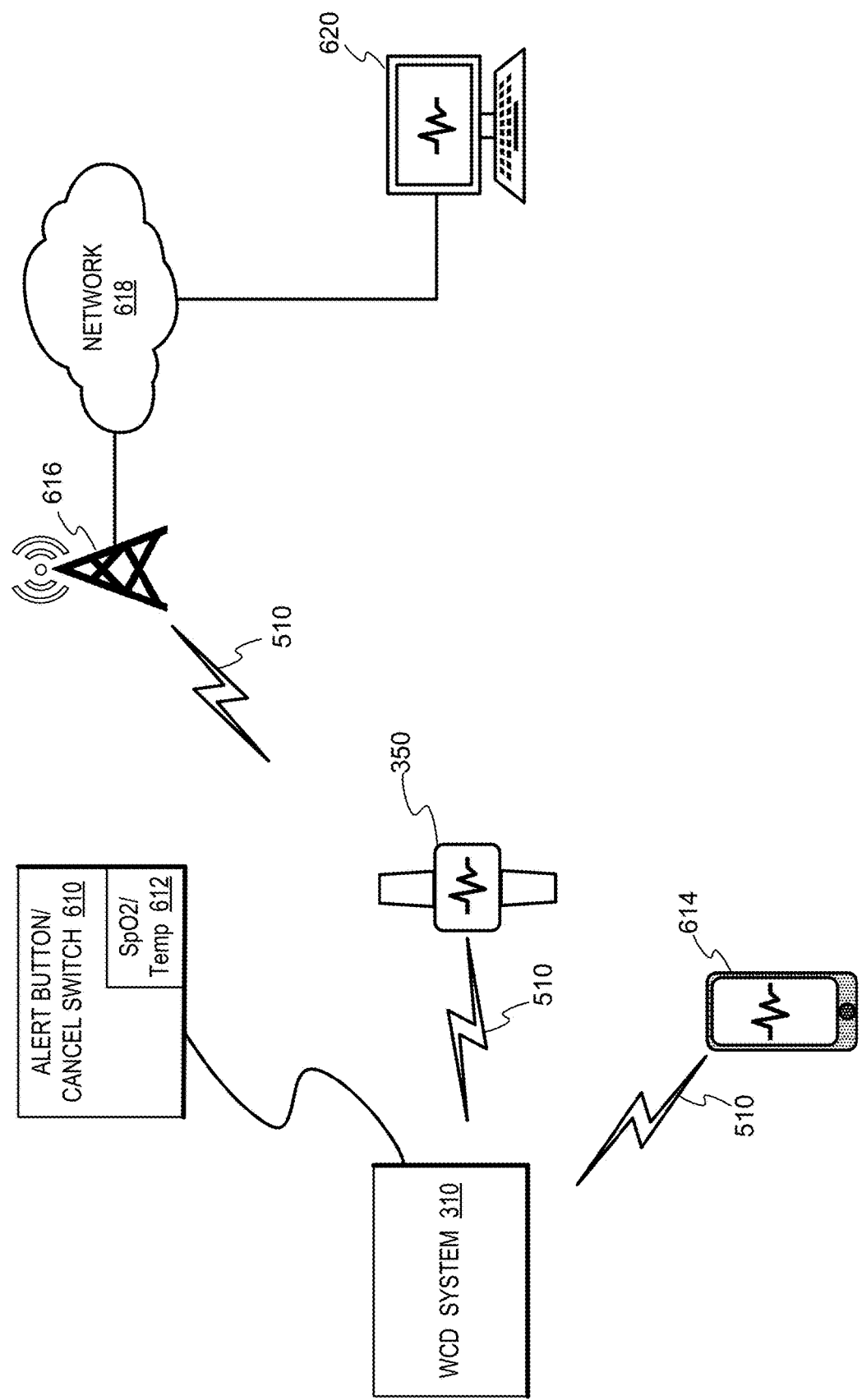
FIG. 6 is a diagram of example system in which blood pressure data and SpO2 data can be collected with a WCD and saved or transmitted to a remote device via a network in accordance with one or more embodiments.

In accordance with one or more embodiments, NIPB monitor 350) can communicate with external defibrillator 500, for example via a wireless communication link 510 in some embodiments. In other embodiments, NIBP monitor 350) also can communicate with external defibrillator 500 via a wired communication link, and the scope of the disclosed subject matter is not limited in this respect. Various example embodiments of how NIBP monitor 350 can communicate with WCD system 310 are shown in and described with respect to FIG. 6, below:

FIG. 6 is a diagram of example system in which data including blood pressure data and SpO2 data can be collected with a WCD and saved or transmitted to a remote device via a network in accordance with one or more embodiments. FIG. 6 illustrates one example of how data collected from medical devices and non-medical devices can be uploaded over a network to a remote device such as care station server 122 of FIG. 1 and FIG. 2, and how information can be downloaded to the medical devices and non-medical devices. As shown in FIG. 6, NIBP monitor 350) can obtain blood pressure data and/or peripheral capillary oxygen saturation (SpO2) data from a patient 382 and can transmit the collected patient data to WCD system 310 via wireless communication link 310. In some embodiments, NIBP monitor 350 can be worn somewhere on the patient's body such as on a wrist, and ankle, and so on. In some embodiments, an SpO2 sensor and/or temperature sensor 612 may be located in the alert button, or cancel or stop switch, 610 that is coupled with the WCD system 310. Since SpO2 sensors typically are configured to take a reading from a patient's fingertip, this type of sensor can easily be incorporated into the alert button 612 mechanism or housing. Additionally, in some embodiments, one or more sensors can be integrated into an external device such as a smartphone 614 that is capable of collecting patient data and transmitting the patient data to WCD system 310. The WCD system 310 may include storage such as memory 438 of FIG. 4 in which collected patient data can be stored for later retrieval and analysis by medical personnel working with the patient 382. For example, memory 438 may include a secure digital (SD) card or multimedia card (MMC) that is capable of being removably insertable into WCD system 310 and which can be removed by the medical personnel for retrieval of the collected patient data. In other embodiments, the patient data can be collected and stored in a memory 438 of WCD 310 which can be transmitted to the device 620 of remotely located medical personnel, for example via a radio access network (RAN) 616 coupled to device 620 via a network 618 which may be, for example, the Internet. The device 620 of the medical personnel may comprise a personal computer, a server, a terminal, tablet, and so on that is capable of receiving, storing, accessing, displaying, and/or analyzing the patient data collected by NIBP monitor 350, SpO2 and/or temperature sensor 612, or smartphone 614, and so on.

In some embodiments, NIBP monitor 350 and/or smartphone 614 may include circuitry and/or software to transmit the collected patient data to device 620 via RAN 616. For example, NIBP monitor 350 and/or smartphone 614 can include a cellular modem to communicate with RAN 616 wherein RAN 616 is part of a cellular network, for example operating in accordance with a Third Generation Partnership Project (3GPP) standard. In other embodiments, RAN 616 can be a wireless router that is part of a Wi-Fi or IEEE 802.11x network that is capable of communicating with device 620 via network 618.

In one or more embodiments, an SpO2 sensor such as SpO2 sensor 412 can be powered by a hub portion of the WCD system 310 for example the outside monitoring device 380 of FIG. 3. In some embodiments the outside monitoring device 380 provides connections and circuitry to the sensing electrodes 409 and the sensor port 419 as shown in FIG. 4, wherein at least some of the circuitry of defibrillator 400 may be contained in the outside monitoring device 380 or hub. In those embodiments, sensor port 419 and measurement circuit 420 may be disposed in the hub and can include an analog preamplifier and other analog circuitry to receive analog signals from the patient via the sensing electrodes 409, for example ECG signals. The measurement circuit 420 can include analog-to-digital converts (ADCs) to convert analog signals received via sensing port 419 to digital signals as digital representations of the analog signals which are provided to processor 430. Furthermore, measurement circuit 420 can include an isolation barrier to isolate the analog signals received via sensor port 419 from the digital signals provided to processor 430. Such an isolation barrier may include an opto-isolator or optocoupler and/or an isolation transformer. Thus, the hub can include an isolated side to isolate the ECG signals from the rest of the circuitry of WCD system 310. The SpO2 sensor 612 can connect to the sensor port 419 and be powered from the isolated side of the hub to provide an analog signal connected to an available channel of the measurement circuit 420. For example, measurement circuit 420 can receive four ECG signals from four ECG sensing electrodes 409 and have an additional channel that is used as a common mode signal, referred to as a right-leg drive (RLD). The SpO2 sensor may be connected to the RLD channel of the measurement circuit 420 for the common mode signal that is otherwise not used for recording data. This arrangement would facilitate pulse transit time (PTT) calculations the SpO2 value would be directly correlated to the ECG.

In another embodiment, as shown in FIG. 6 an SpO2 sensor can be incorporated into the alert button 610. In this arrangement, when a reading is needed the patient is prompted to put his or her finger on the SpO2 sensor of the alert button 610. Signals can be digitized at the sensor 412 and transmitted directly to processor 430, which may comprise a system on module (SOM), over a serial communication bus.

In yet another embodiment, an SpO2 sensor can comprise a separate SpO2 and/or temperature sensor 612 that that is cabled from the hub, separate from the alert button 610, in a manner that is similar to the way that the alert button 610 is cabled to the hub but applied to the patient's body in an area that can provide continuous SpO2 and/or temperature measurements. In such embodiments, the additional SpO2 and/or temperature sensors 612 can be powered from the same power supply voltage, for example 3.9 V, that supplies power to the hub. In addition, a communication bus can be multiplexed onto squib fire wires so as not to add additional wires and/or pins to the Therapy Cable and/or Plug of the hub. The measurement circuit 420 includes the hardware capability to measure impedance and respiration in combination with software running on processor 430. In other embodiments, SpO2 and/or temperature sensors 612 can be self-powered, for example from a separate batter, and can communicate with either the external defibrillator 300, sometimes referred to as the monitor, or the outside monitoring device 380, sometimes referred to as the hub, over a lower or medium range wireless communication link such as BLUETOOTH, ZIGBEE, or Wi-Fi, and so on.

The patient data relating to blood pressure, heart rate/pulse, SpO2, and/or temperature can be collected by any one or more of the NIBP monitor 350, SpO2 and/or temperature sensor 612, and/or smartphone 614 can be provided to WCD system 310 analysis that would help medical personnel to understand the patient's health and status during an episode detected by WCD system 310, for example wherein such patient data can be supplemental to the data collected directly by WCD 310 to detect an episode and to make a shock/no-shock decision for the episode. In other embodiments, the collected patient data can be fed into WCD system 310 to provide additional parameters with which an episode can be identified and/or to assist WCD system 310 in making shock/no-shock decisions. The usage of the collected patient data with the monitors and sensors of FIG. 6 can be as shown in and described with respect to FIG. 1 and FIG. 2, above.

Figure 7:
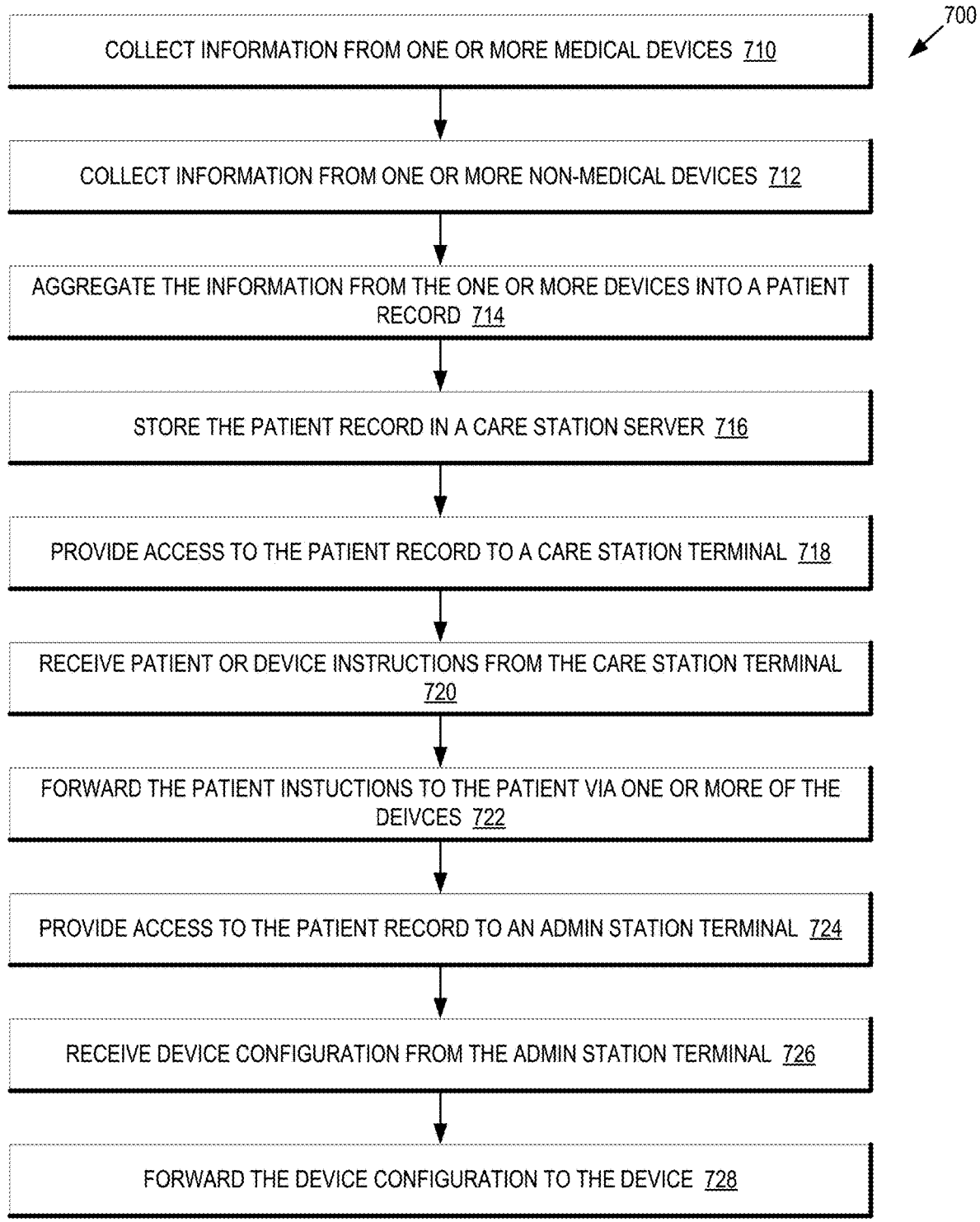
FIG. 7 is a flow diagram of a method for a care station server to aggregate data from multiple medical devices and multiple non-medical devices in accordance with one or more embodiments.

Referring now to FIG. 7, a flow diagram of a method for a care station server to aggregate data from multiple medical devices and multiple non-medical devices in accordance with one or more embodiments. Although FIG. 7 shows one particular order and number of operations for method 700, various other orders or numbers of operations may be provided in alternative embodiments, and the scope of the disclosed subject matter is not limited in these respects. Method 700 illustrates one example of how care station server 122 of FIG. 1 can aggregate data from one or more medical devices or one or more non-medical devices, and how the aggregated data can be accessed by a care station terminal 126 or an admin station terminal 128. At operation 710, care station server 122 can collect information from one or more of the medical devices shown in FIG. 1. At operation 712, care station server 712 can collect information from one or more of the non-medical devices shown in FIG. 1. The collected information can be aggregated into a patient record 124 at operation 714 for a particular user or patient wearing or otherwise using the one or more devices. The patient record 124 can be stored in on or more storage devices in or otherwise coupled with or accessible by care station server 124. This arrangement allows the station server 124 to provide access at operation 718 to the patient record 124 by a care station terminal 126.

When the care station terminal 126 has access to the patient record 124, the operator of the care station terminal 126 can monitor the patient based on the data provided by the one or more devices. For example, if one of the devices is a blood pressure monitor, the operation of the care station terminal 126 can determine if the patient's blood pressure is being maintained within a desired range over a course of a period of time during which the blood pressure monitor is taking one or more blood pressure readings. Similarly, if one of the devices is a wearable cardioverter defibrillator (WCD) as described herein, the operator of the care station terminal 124 can determine whether any therapeutic shocks were applied to the patient by the WCD. If the patient record 124 also includes blood pressure data collected by a blood pressure monitor, the operator of the care station terminal 126 can review the blood pressure data at the time that one or more therapeutic shocks were applied by the WCD to confirm whether the therapeutic shocks were appropriate based on the blood pressure readings by the blood pressure monitors. Using aggregated data from multiple devices in this manner or in a similar manner can allow the operator to cross-check the operation of one device against another to ensure proper operation of both devices. At operation 720, the operator of the care station terminal 126 can provide instructions to the care station server 122 to be delivered to the patient for the patient or how the patient uses a particular device. For example, the instructions can include instructions to change a behavior of the patient such as reduce an amount of the patient's physical activity or to change the dose of a particular medicine, or to change a parameter on one or more of the devices such as to increase the frequency at which a blood pressure monitor takes blood pressure readings. These instructions can also include instructing the patient to swap out one of the devices for a new device. At operation 722, the care station server 122 can forward the instructions received from the care station server 122 to the patient via one or more of the devices 722, for example to the patient's computer, smartphone, smart watch, or tablet.

At operation 724, the care station server 122 can provide access to the patient record 124 to an admin station terminal 128. The operator of the admin station terminal 128 can provide administrative or technical support for the patient and for one or more of the devices used by the patient. For example, the operation of the admin station terminal 128 can review the patient record 124 to ensure that the devices are providing proper and accurate readings of the patient physiological parameters that the devices are monitoring. For example, the patient's blood pressure readings from a blood pressure monitor device can be reviewed to determine that the readings are good and that the blood pressure monitor is being worn properly. If the readings are bad, the operator of the admin terminal 128 can determine whether the monitor is properly configured, has sufficient battery charge, and so on. In addition, the operator of the admin station terminal 128 can ensure that the device have the necessary configurations and permissions to connect with the care station server 122 and to access and update the patient record 124. At operation 726, any needed permissions or device configurations can be provided from the admin station terminal 128 to the care station terminal 122, and at operation 728 the care station terminal 728 can forward the permissions or configurations to the particular device of the patient.

Figure 8:
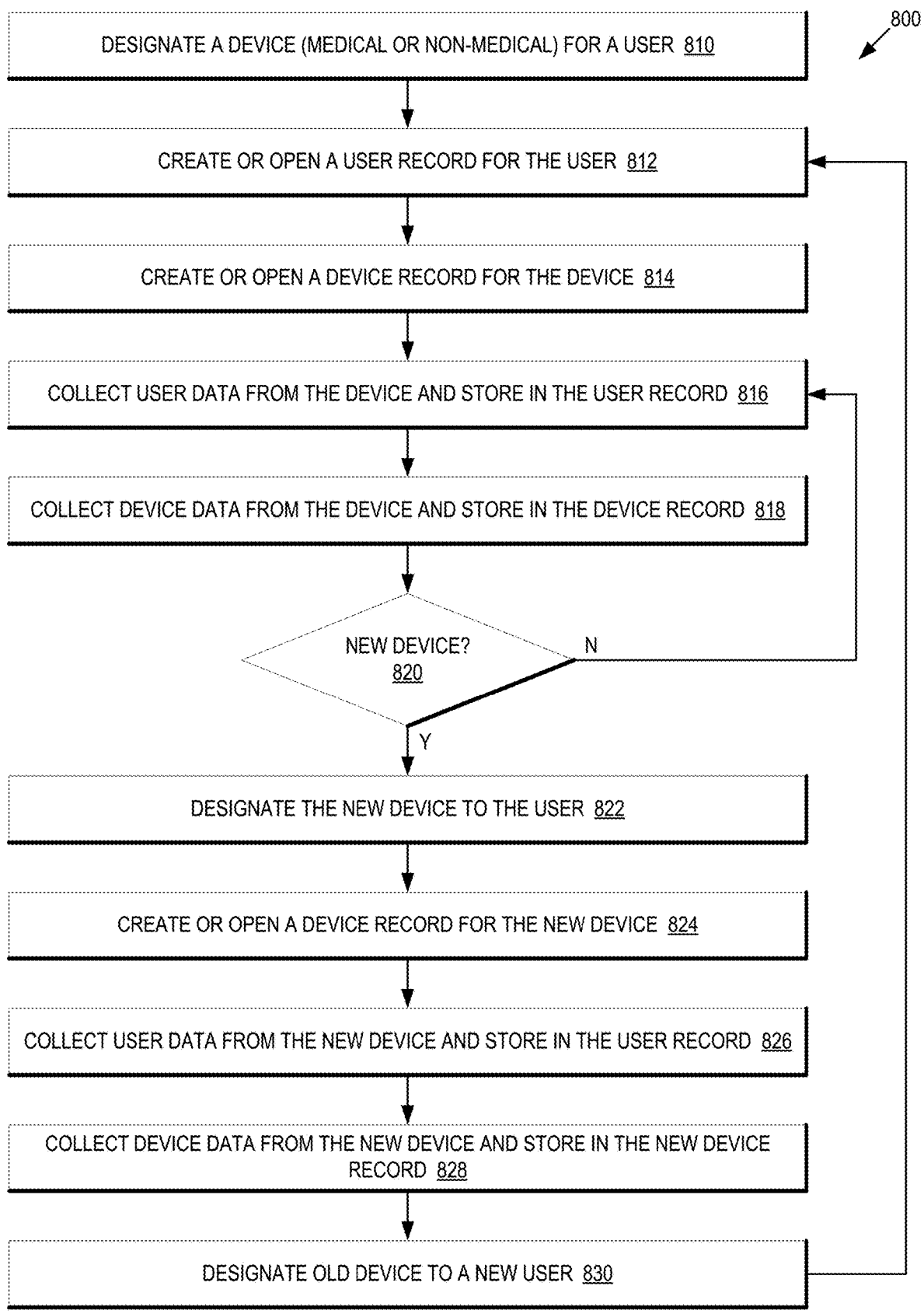
FIG. 8 is a flow diagram of a method for obtaining data from two or more medical devices for two or more patients in accordance with one or more embodiments.

FIG. 8 is a flow diagram of a method for obtaining and managing data from two or more medical devices for two or more patients in accordance with one or more embodiments. Although FIG. 8 shows one particular order and number of operations for method 800, various other orders or numbers of operations may be provided in alternative embodiments, and the scope of the disclosed subject matter is not limited in these respects. Method 800 illustrates one example of how care station server 122 of FIG. 2 can store data from two or more medical devices for multiple patients. At operation 810, care station server 122 can designate a medical device or a non-medical device for a user or patient. The care station server 122 can then create a new record or open a previously existing record for the user at operation 812. Similarly, at operation 814 the care station server 122 can create a new record or open a currently existing record for the designated device. The device can collect user data during its operation which can be uploaded to the care station server 122 to be collected and stored in the user record at operation 816. Likewise, the device can provide device data regarding the performance and operation of the device by uploading the device data to the care station server 122 to be collected and stored in the device record at operation 818.

At decision block 820, a determination can be made whether a new device is being used by the user. For example, a new device can be added to the current number of devices being used by the user. Alternatively, a new device can replace one or more currently existing devices being used by the user. If there are no new devices, method 800 can continue to collect user data at operation 816 and can continue to collect device data at operation 818. If a new device is provided, care station server 122 can designate the new device to the user at operation 822. At operation 824, the care station server 122 can then create a new device record if one currently does not exist, or can open an existing device record for the new device if there is an existing device record for the new device. At operation 826, user data can be collected from the new device and stored in the user record. At operation 828, device data can be collected from the new device and stored in the device record for the new device. Optionally, a new user can use an old device that was replaced by the new device. In this situation, the old device can be designated to the new user at operation 830, and method 800 can continue at operation 812 for the new user and the old device. Using method 800, care station server 122 can collect data from multiple devices for multiple users. Devices can be assigned to one of the users, and can be later assigned to one or more new users. A new device can be assigned to a user, and the collected data from the new device can be used to update the user's record so that the user's record reflects an aggregation of data from multiple devices. Similarly, device data for a device can reflect an aggregation of data from multiple users so that the device's record reflects an aggregation of data from multiple users. It should be noted that these are merely examples of how method 800 can be applied to multiple users or multiple devices, and the scope of the disclosed subject matter is not limited in these respects.

Figure 9:
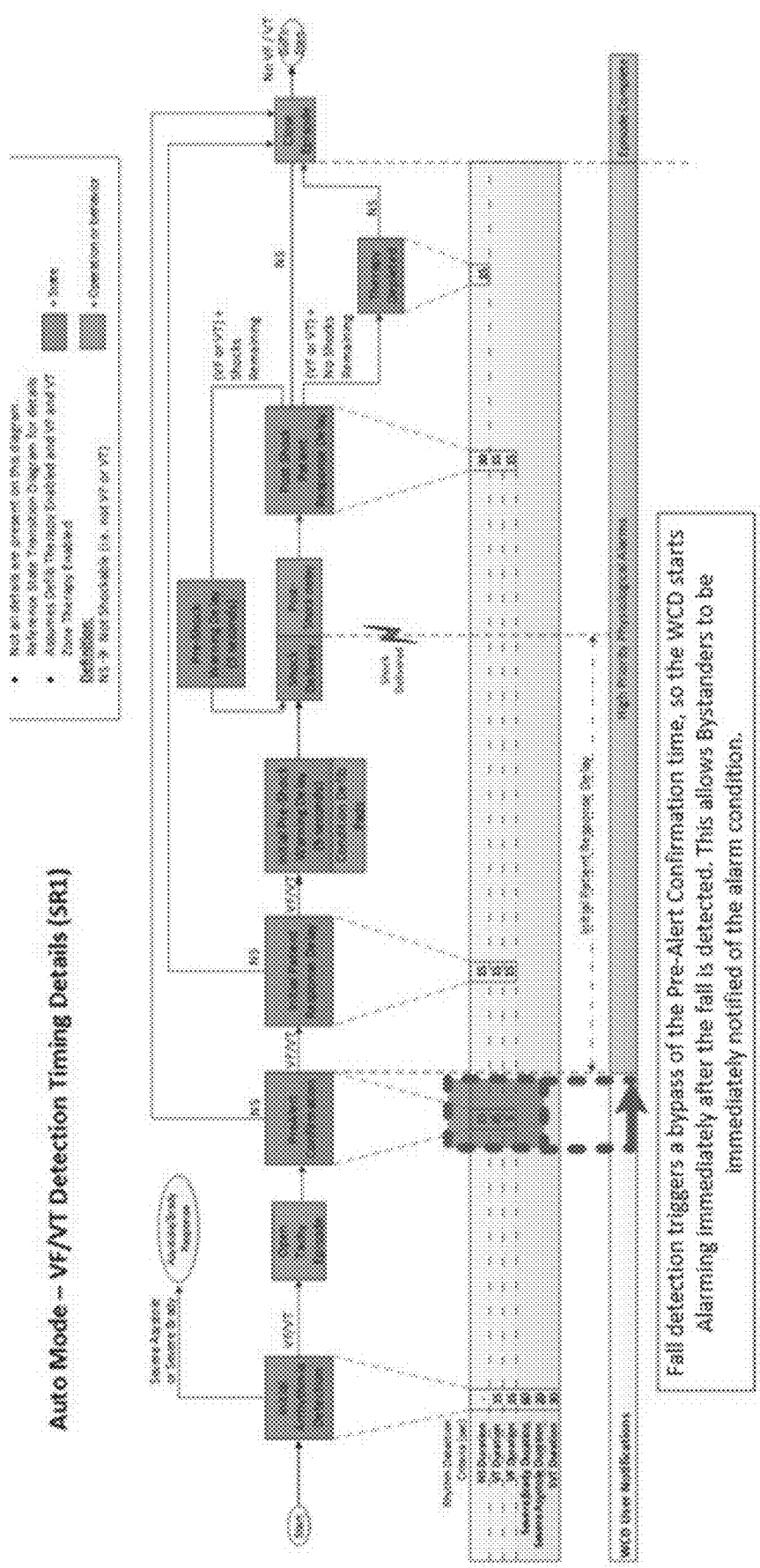
FIG. 9 is a diagram of fall detection as implanted by a medical device such as a wearable cardioverter defibrillator (WCD) in accordance with one or more embodiments.

Referring now to FIG. 9, a diagram of fall detection as implanted by a medical device such as a wearable cardioverter defibrillator (WCD) in accordance with one or more embodiments will be discussed. WCDs are typically configured to monitor the patient's ECG for arrhythmias that may require therapy such as a defibrillation shock or pacing shocks. When such an arrhythmia is initially detected, typical WCDs are configured to continue monitoring for a set time to "confirm" that the arrhythmia requires therapy. A set time prior to providing the therapy, typical WCDs provide an alarm to the patient so that if the patient is conscious (i.e., the WCD made a false positive shock decision), the Patient can divert the upcoming therapy. Such alarms would typically be the only way a bystander would know that the WCD is performing a rhythm analysis.

One or more embodiments herein are directed to a WCD that is configured to: (a) detect when the Patient wearing the WCD has fallen; and (b) take an appropriate action in response to the fall detection. For example, a Patient experiencing an arrhythmia may collapse to the ground while the WCD's rhythm analysis is being performed. Bystanders who see the collapsed Patient may not know that the Patient is wearing a WCD and that the rhythm analysis is ongoing. Thus, a bystander may try to help the Patient (e.g., moving the patient, performing CPR, etc.). Such intervention can cause noise artifacts in the ECG signals, which can interfere with the rhythm analysis and delay or prevent needed treatment provided by the WCD. The FIG. 9 shows a process for providing treatment, according to embodiments.

As can be seen in FIG. 9, in some embodiments the WCD is configured with an Initial Detection phase in which 15 seconds of a ventricular arrhythmia or 20-60 seconds of asystole/brady arrhythmia triggers the opening of an episode. This is followed by a "silent" confirmation period in which the WCD is configured to confirm an arrhythmia prior to issuing High Priority Physiological Alarms. In embodiments, this confirmation period is nominally 5 seconds for ventricular fibrillation (VF) and 45 seconds for ventricular tachycardia (VT), but can be extended for a longer time to satisfy the criteria of the arrhythmia.

In embodiments, the High Priority Physiological Alarms can serve the following purposes: (1) Allow a conscious Patient to divert a shock (in the case of a false detection) and, (2) Inform Bystanders that an event is occurring and they should not interfere (e.g. "Preparing to shock . . . . Do not touch the Patient . . . ").

If a Patient experiences an arrhythmia, the Patient may collapse to the ground while the WCD is performing silent analysis to confirm the detected arrhythmia. This could potentially take more than 60 seconds before a High Priority Physiological Alarm is issued. In conventional WCDs during this silent period, bystanders are given no indication by the Assure WCD that there is ongoing analysis by the WCD. Thus, good Samaritans may begin cardiopulmonary resuscitation (CPR) or otherwise interfere with the system and prevent analysis, thereby impeding treatment by the WCD.

In contrast, embodiments of WCDs according to the present disclosure can be configured to detect whether the Patient has fallen. In some embodiments, the WCD includes one or more accelerometers in a WCD component coupled to the Patients body. For example, some WCDs have a garment or support structure that is worn by the Patient: the accelerometer(s) may be integrated or attached to the garment. In other embodiments, the WCD may have an electronics module or other electronics interface components integrated or attached to the support structure, which components include an impact detector, accelerometer or other sensor(s) that can be used to detect whether the Patient has fallen. While the Patient is wearing the WCD embodiments, the signals from one or more of these sensors are monitored to determine when a fall occurs.

In other embodiments, the WCD with built-in fall detection is configured to generate a remote alert to a service center (similar to other "Help, I Fell" devices). In some embodiments, the WCD can be configured to so that if a fall is detected during "Pre-Alert Confirmation" (see FIG. 9), the WCD is configured to immediately start High Priority Physiological Alarms. These alarms would immediately warn bystanders not to touch the patient or otherwise interfere with the WCD in completing the rhythm analysis. In some embodiments, in response to a fall being detected, the alarms may also include prompts to bystanders to call for help (e.g., call 911).

In some embodiments, the fall-triggered High Priority Physiological Alarm include these following behaviors: (1) Cause the WCD to immediately transition to Initial Patient Response Delay, which eliminates the extra confirmation time, (2) Cause an alarm to issue during Pre-Alert Confirmation. In some embodiments this alarm could be an earlier extension of the High Priority Physiological Alarm sequence, while in other embodiments it could be a different informative alarm (e.g. "This Patient is wearing a Medical Device. Do not touch the Patient . . . ").

Embodiments described herein can provide one or more of the following benefits: a higher sense of protection for the patient: reduction of bystander interference while the WCD is analyzing the patient's ECG: or quicker treatment of a Patient in need of treatment by bypassing the remaining Pre-Alert Confirmation time.

The following are example implementations of the subject matter described herein. It should be noted that any of the examples and the variations thereof described herein may be used in any permutation or combination of any other one or more examples or variations, although the scope of the disclosed subject matter is not limited in these respects. In a first example, a wearable cardioverter defibrillator (WCD) system can comprise a support structure configured to be worn by a patient, a patient ECG sensor configured to be coupled to the patient when the patient is wearing the support structure, a patient fall sensor to be coupled to the patient: a memory, and a processor communicatively coupled to the patient ECG sensor and the patient fall sensor and configured to perform an action in response to a patient falling. In a second example, the action comprises providing an indication to bystanders to avoid touching and/or moving the patient. In a third example, the action comprises escalating a therapy sequence of the WCD system. In a fourth example, the action comprises providing an alert to a remote receiver.

Although the claimed subject matter has been described with a certain degree of particularity, it should be recognized that elements thereof may be altered by persons skilled in the art without departing from the spirit and/or scope of claimed subject matter. It is believed that the subject matter pertaining to analysis and presentation of aggregated patient and device data within a system that includes a medical device and many of its attendant utilities will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A method to aggregate information from a plurality of wearable cardioverter defibrillators (WCDs), wherein the WCDs comprise sensing electrodes, a processor coupled to the sensing electrodes, an energy storage module, a discharge circuit, and defibrillation electrodes, the method comprising:
collecting information from the plurality of WCDs used by a patient, wherein each WCD is customized for the patient;
wherein:
information is collected from a first WCD including a first cardiovascular record for the patient measured with the first WCD, wherein the first WCD is worn by the patient over a first period;
information is collected from a second WCD including a second cardiovascular record for the patient measured with the second WCD, wherein the second WCD is worn by the patient over a second period subsequent to the first period;
aggregating the information from the first WCD and the second WCD into a single patient record for the patient, wherein the single patient record includes a combined cardiovascular record for the patient based at least in part on the first cardiovascular record and the second cardiovascular record;
storing the patient record to be accessible by a care station server;
providing access to the patient record via the care station server;
sending a parameter change to the second WCD based at least in part on the combined cardiovascular record, wherein the parameter change includes changing a cardiovascular measurement obtained by the second WCD, and the cardiovascular measurement is used to determine, with the processor of the second WCD, whether to deliver a therapeutic electrical charge to the patient using the second WCD; and
delivering the therapeutic electrical charge to the patient with the energy storage module, discharge circuit, and the defibrillation electrodes of the second WCD based on the changed cardiovascular measurement.

2. The method of claim 1, wherein the patient record is accessible via the care station server from a care station terminal.

3. The method of claim 2, further comprising: receiving an instruction for the patient from the care station terminal, and forwarding the instruction to one of the plurality of WCDs to be received by the patient.

4. The method of claim 1, wherein the patient record is accessible via the care station server from an admin station terminal.

5. The method of claim 4, further comprising: receiving a WCD configuration from the admin station terminal, and forwarding the WCD configuration to the corresponding one of the plurality of WCDs.

6. The method of claim 1, wherein the patient record is stored in the care station server.

7. The method of claim 1, wherein the patient record is stored external to the care station server.

8. The method of claim 1, wherein the information is collected from two or more WCDs used by the patient, and the information from the WCDs is aggregated into the patient record to allow operation of one of the WCDs to be compared with operation of another one of the WCDs.

9. The method of claim 1, further comprising: collecting information from one or more non-medical devices, and aggregating the non-medical device information with the WCD information in the patient record.

10. The method of claim 1, wherein the patient wears a first WCD of the plurality of WCDs for a first period of time, and a second WCD of the plurality of WCDs for a second period of time responsive to the first WCD having an error condition, and the second WCD replaces the first WCD.

11. A method to collect data from a plurality of wearable cardioverter defibrillators (WCDs), wherein the WCDs comprise sensing electrodes, a processor coupled to the sensing electrodes, an energy storage module, a discharge circuit, and defibrillation electrodes, the method comprising:
designating a first WCD for a first patient;
collecting patient data for the first patient with the first WCD;
storing the patient data for the first patient from the first WCD in a first patient record;
designating a second WCD for the first patient;
collecting patient data for the first patient with the second WCD;
storing the patient data for the first patient from the second WCD in the first patient record, wherein the patient data in the first patient record comprises an aggregation of data from the first WCD and the second WCD, and wherein the first patient record is accessible by a care station server;
providing access to the first patient record including the aggregation of data via a care station server;
sending a parameter change to the second WCD based at least in part on the aggregated data, wherein the parameter change includes changing a cardiovascular measurement obtained by the second WCD, and the cardiovascular measurement is used to determine, with the processor of the second WCD, whether to deliver a therapeutic electrical charge to the first patient using the second WCD; and
delivering the therapeutic electrical charge to the first patient with the energy storage module, discharge circuit, and the defibrillation electrodes of the second WCD based on the changed cardiovascular measurement.

12. The method of claim 11, further comprising: designating the first WCD for a second patient; collecting patient data for the second patient with the first WCD; and storing the patient data for the second patient from the first WCD in a second patient record.

13. The method of claim 11, wherein the first WCD and the second WCD are both configured to be used interchangeably by the first patient.

14. The method of claim 11, wherein the second WCD replaces the first WCD.

15. A care station server to aggregate information from one or more medical devices including a wearable cardioverter defibrillator (WCD), wherein the WCD comprises sensing electrodes, a WCD processor coupled to the sensing electrodes, an energy storage module, a discharge circuit, and defibrillation electrodes, the care station server comprising:
- a care station server processor and a memory coupled to the care station server processor, wherein instructions in the memory configure the care station server processor to:
  - collect information from one or more of the medical devices including the WCD used by a patient, wherein the WCD is customized for the patient;
  - wherein:
    - information is collected from a first one of the medical devices including a first cardiovascular record for the patient measured with the first one of the medical devices, wherein the first one of the medical devices is worn by the patient over a first period;
    - information is collected from a second one of the medical devices including a second cardiovascular record for the patient measured with the second one of the medical devices, wherein the second one of the medical devices is worn by the patient over a second period subsequent to the first period;
  - aggregate the information from the first one of the medical devices and the second one of the medical devices into a single patient record for the patient, wherein the single patient record includes a combined cardiovascular record for the patient based at least in part on the first cardiovascular record and the second cardiovascular record;
  - store the patient record including the aggregated information to be accessible by the care station server processor of the care station server;
  - provide access to the patient record via the care station server processor of the care station server; and
  - send a parameter change to the second one of the medical devices based at least in part on the combined cardiovascular record, wherein the parameter change includes changing a cardiovascular measurement obtained by the second one of the medical devices, and the cardiovascular measurement is used by the WCD to determine, with the WCD processor, whether to provide a therapeutic electrical charge to the patient; and
  - delivering the therapeutic electrical charge to the patient with the energy storage module, discharge circuit, and the defibrillation electrodes of the WCD based on the changed cardiovascular measurement.

16. The care station server of claim 15, wherein the patient record is accessible via the care station server processor of the care station server from a care station terminal.

17. The care station server of claim 16, wherein the care station server processor is further configured to: receive an instruction for the patient from the care station terminal, and forward the instruction to one of the medical devices including the WCD to be received by the patient.

18. The care station server of claim 15, wherein the patient record is accessible via the care station server processor from an admin station terminal.

19. The care station server of claim 18, wherein the care station server processor is further configured to: receive a device configuration from the admin station terminal for the one or more medical devices including a WCD, and forward the device configuration to the corresponding one of the medical devices.

20. The care station server of claim 15, wherein performance of the one or more medical devices including the WCD as used by the patient can be monitored remotely via the patient record.

\* \* \* \* \*